(12) United States Patent
Lee et al.

(10) Patent No.: US 6,168,806 B1
(45) Date of Patent: Jan. 2, 2001

(54) ORALLY ADMINISTRABLE NIFEDIPINE PELLET AND PROCESS FOR THE PREPARATION THEREOF

(76) Inventors: Fang-Yu Lee; Shan-Chiung Chen; Han-Chiang Kuo, all of 1191 Sec 1, Chung-shan Rd., Tachia, Taichung (TW)

(*) Notice: Under 35 U.S.C. 154(b), the term of this patent shall be extended for 0 days.

(21) Appl. No.: 09/263,693

(22) Filed: Mar. 5, 1999

(51) Int. Cl.$^7$ .............................. A61K 9/16; A61K 9/14
(52) U.S. Cl. ..................... 424/493; 424/489; 424/490; 424/494; 424/495; 424/497; 427/2.14; 514/356; 514/962
(58) Field of Search .................. 424/489, 490, 424/493, 494, 495, 497, 451; 514/962, 356; 427/2.14

(56) References Cited

U.S. PATENT DOCUMENTS

| | | | |
|---|---|---|---|
| 4,562,069 | 12/1985 | Hegasy et al. | 424/19 |
| 4,665,081 | 5/1987 | Doi et al. | 514/356 |
| 4,814,175 | 3/1989 | Tack et al. | 424/453 |
| 4,904,699 | 2/1990 | Bauer | 514/972 |
| 4,981,683 | 1/1991 | Hegasy | 424/80 |
| 5,145,683 | 9/1992 | Rhodes | 424/451 |
| 5,200,192 | 4/1993 | Wimmer | 424/455 |
| 5,594,013 | 1/1997 | Trigger | 514/356 |
| 5,871,776 | * 2/1999 | Mehta . | |

OTHER PUBLICATIONS

Ho et al., The Preparation and Characterization of Solid Dispersions on Pellets Using a Fluidized–Bed System, Int. J. Pharm, vol. 139, No. 1, 2, pp. 223–229, 1996.*

* cited by examiner

*Primary Examiner*—Thurman K. Page
*Assistant Examiner*—Brian K. Seidleck
(74) *Attorney, Agent, or Firm*—Fei-Fei Chao; Venable, Baetjer, Howard & Civiletti, LLP

(57) ABSTRACT

The present invention relates to a fast-release as well as a prolonged release type of nifedipine pellets and the process for the preparation thereof. The fast-release type of nifedipine pellets comprises a particulate core which is covered by a nifedipine coating layer. The particulate core comprises water-soluble or water-insoluble excipient(s) and a pharmacologically acceptable carrier. The nifedipine coating layer comprises an effective amount of nifedipine dissolved in organic solvent(s). This nifedipine coating layer can further be mixed with a suspension which comprises an adhesive, an emulsifier, and a dispersant. The preferred composition of the fast-release type of nifedipine includes 20–70% of the particulate core, 3–15% of nifedipine, 1–20% of emulsifier, 1–20% of adhesive, and 1–30% of dispersant. The prolonged-release type of nifedipine pellets comprises, in addition to the particulate core and the nifedipine coating layer, a surface coating layer which is made of at lease one consisting of hydroxypropylcellulose, hydroxypropylmethylcellulose and ethylcellulose. This surface coating layer further comprises a plasticizer which is selected from the group consisting of triethylcitrate, triacetin, and diethyl phthalate.

22 Claims, 2 Drawing Sheets

ORALLY ADMINISTRABLE NIFEDIPINE PELLET AND PROCESS FOR THE PREPARATION THEREOF

I. FIELD OF THE INVENTION

The present invention relates to an orally administrable nifedipine pellet and a process for the preparation thereof. In particular, the present invention relates to a nifedipine-containing pellet which provides for a fast as well as a prolonged release pattern of nifedipine upon oral administration, and the process for the preparation thereof.

II. BACKGROUND OF THE INVENTION

Nifedipine, 1,4-dihydro-2,6-dimethyl-4-(2-nitrophenyl) pyridinedicarboxylic acid dimethyl ester, is a known active compound from the substance class of the dihydropyridines, which affects the circulation. Nifedipine has been widely used as a coronary vasodilator or calcium channel antagonist in treatment of coronary insufficiency and angina.

Nifedipine is very poorly soluble in water. Nifedipine will dissolve in water only to an extent of about 1:200,000 and is sparingly soluble in ethanol and in glycerol but more readily soluble in chloroform and acetone. Owing to its low solubility, nifedipine has in most cases been embedded in soluble, hydrophilic polymers such as polyethylene glycol (PEG), polyvinylpyrrolidone (PVP) or cellulose ethers. This gives rise to solid solutions if it dissolves in the molten form of, for example, PEG, or to coprecipitates, for example, in PVP, with suitable solvents and then precipitated in a very finely divided form by removal of the solvents.

Nifedipine is generally delivered in two patterns, i.e., a quick release form and a slow release form, based upon the types of medical treatments. For instance, for the acute treatment of angina, it is desirable to attain relatively high nifedipine concentrations in plasma quickly and a fast release preparation of nifedipine is thus preferred. On the other hand, for the treatment of hypertension, it is more desirable to maintain plasma nifedipine concentrations within a much lower concentration range and a slow release preparation of nifedipine is thus preferred.

The fast release form of nifedipine is currently served by a preparation consisting of an aqueous or aqueous alcoholic solution of nifedipine having a polyalkylene glycol and/or a polyoxyethylene ester component within a soft gelatin capsule. (See e.g., U.S. Pat. Nos. 4,978,533 and 5,200,192). The slow release form of nifedipine is currently available by dissolving microcrystalline particles of nifedipine in the presence of polyvinyl-pyrrolidone (PVP). (See e.g., U.S. Pat. No. 5,145,683). However, both of the above mentioned forms of nifedipine are difficult to prepare, which significantly affect the manufacturing costs for production.

In the invention to be presented below, a new form of nifedipine delivery system will be introduced. This new nifedipine delivery system is in the form of an orally administrable nifedipine pellet which can be encapsulated for easy uptake. This new nifedipine pellet can function as both of the fast and the slow release forms of nifedipine, depending upon the compositional and structural configuration of the pellet. Also, because this new nifedipine pellet can be manufactured by any conventional particle coating devices such as Glatt and Huttlin, it has the advantages of cost effectiveness.

III. SUMMARY OF THE INVENTION

The first embodiment of the present invention provides a fast release form of nifedipine pellet which comprises (1) a particulate core, and (2) a nifedipine coating layer which is coated onto said particulate core. This nifedipine pellet can be administered orally.

The particulate core comprises an excipient which can be water-soluble or water-insoluble and a pharmacologically acceptable carrier. The water-soluble excipient comprises at least one selected from the group consisting of mannose, galactose, glucose, fructose, sucrose, lactose, maltose, dextrin, glycogen, and inulin. The water-insoluble excipient is at least one selected from the group consisting of starch, micro-crystalline cellulose, and talc. The preferable pharmacologically acceptable carrier is sucrose.

The nifedipine coating layer comprises an effective amount of nifedipine which is dissolved in organic solvents. The preferable organic solvents include acetone, alcohol, and isopropanol. The preferable organic solvent for dissolving nifedipine contains a mixture of acetone and alcohol in the ratio (vol/vol) of 1:1.1 to 1:4. A 0 to 30% (by volume) of distilled water can be added to the acetone and alcohol mixture.

The nifedipine dissolved in organic solvent can be further mixed with an emulsified dispersing suspension which comprises an emulsifier, an adhesive, and a dispersant. The preferable emulsifier includes poloxamer 188, Tween 80, and sodium lauryl sulfate. The preferable adhesive includes polyvinylpyrrolidone, hydroxypropylcellulose, methylcellulose, and hydroxypropylmethylcellulose. The preferable dispersant includes lactose, sucrose, fructose, maltose, mannose, glucose, and polyethylene glycol (PEG) with molecular weight of 4,000, 6,000, 8,000 and 20,000. Among the various molecular weights of PEG, the most preferable one is PEG 20,000. In the case where the emulsified dispersing suspension is used in forming the nifedipine coating layer, the ratio (by weight) of said particulate core and said nifedipine coating layer is 1: 0.04–0.14% of nifedipine, 1–7% of emulsifier, 0.4–7% of adhesive, 0.9–11% of dispersant, 7–15% of organic solvent, and 4–10% of distilled water. The preferable composition of the nifedipine pellet comprises 20–70% by weight of the particulate core, 3 to 15% by weight of the nifedipine, 1–20% by weight of the emulsifier, 1–20% by weight of the adhesive, and 1–30% by weight of the dispersant.

The second embodiment of the present invention provides a prolonged release form of nifedipine pellet which comprises (1) a particulate core, (2) a nifedipine coating layer which covers the particulate core, and (3) a surface coating layer which covers the nifedipine coating layer.

The chemical compositions of the particulate core and the nifedipine coating layer are the same as those described in the first embodiment. The surface coating layer comprises at least one selected from the group consisting of polyvinylpyrrolidone, hydroxypropylcellulose, hydroxypropylmethylcellulose, and ethylcellulose. This surface coating layer can further comprise at least one selected from the group consisting of triethylcitrate, triacetin, and diethyl phthalate.

The third embodiment of the present invention provides a method for preparing the nifedipine pellet as described in the first and the second embodiments. The method of making the nifedipine pellet described in the first embodiment comprises the steps of: (1) forming a particulate core, and (2) spraying a nifedipine coating layer onto said particulate core. The method of making the nifedipine pellet described in the second embodiment adds a step of spraying a surface coating layer onto the nifedipine coating layer.

The particulate core is made by the steps of: (1) dissolving polyvinylpyrrolidone in an organic solvent (such as isopropanol); (2) mixing said dissolved polyvinylpyrrolidone with distilled water to form an adhesive solution; (3) mixing a pharmacologically acceptable carrier and an excipient in a particle pelletizing device (by rotation); and (4) spraying said adhesive solution via spraying nozzles in the particle pelletizing device onto said pharmacologically acceptable carrier and said excipient. The newly formed particulate core can be further dried via filtered or heated air within the particle pelletizing device. The preferable particle pelletizing devices are the ones manufactured by Glatt or Huttlin.

The method of making the nifedipine coating layer comprises the steps of: (1) dissolving nifedipine in an organic solvent; and (2) spraying said dissolved nifedipine onto said particulate core. The preferred method is to mix the dissolved nifedipine in an emulsified dispersing suspension which is prepared by mixing the adhesive, the emulsifier, and the dispersant together to form a nifedipine coating solution, followed by spraying the nifedipine coating solution onto the particulate core. This process can also be proceeded in any of the conventional particle pelletizing device.

The method of making the surface coating layer comprises the steps of: (1) dissolving a surface coating material in alcohol or distilled water, wherein said surface coating material is at least one selected from the group consisting of polyvinylpyrrolidone, hydroxypropylcellulose, hydroxypropylmethylcellulose, and ethylcellulose; and (2) spraying said alcohol- or distilled water-dissolved surface coating material onto said nifedipine coating layer of said nifedipine pellet. This method can further include a step of adding triethyl citrate, triacetin or diethyl phthalate to the surface coating material.

IV. BRIEF DESCRIPTION OF THE DRAWING

V. DETAILED DESCRIPTION OF THE EMBODIMENTS

Figure 1:
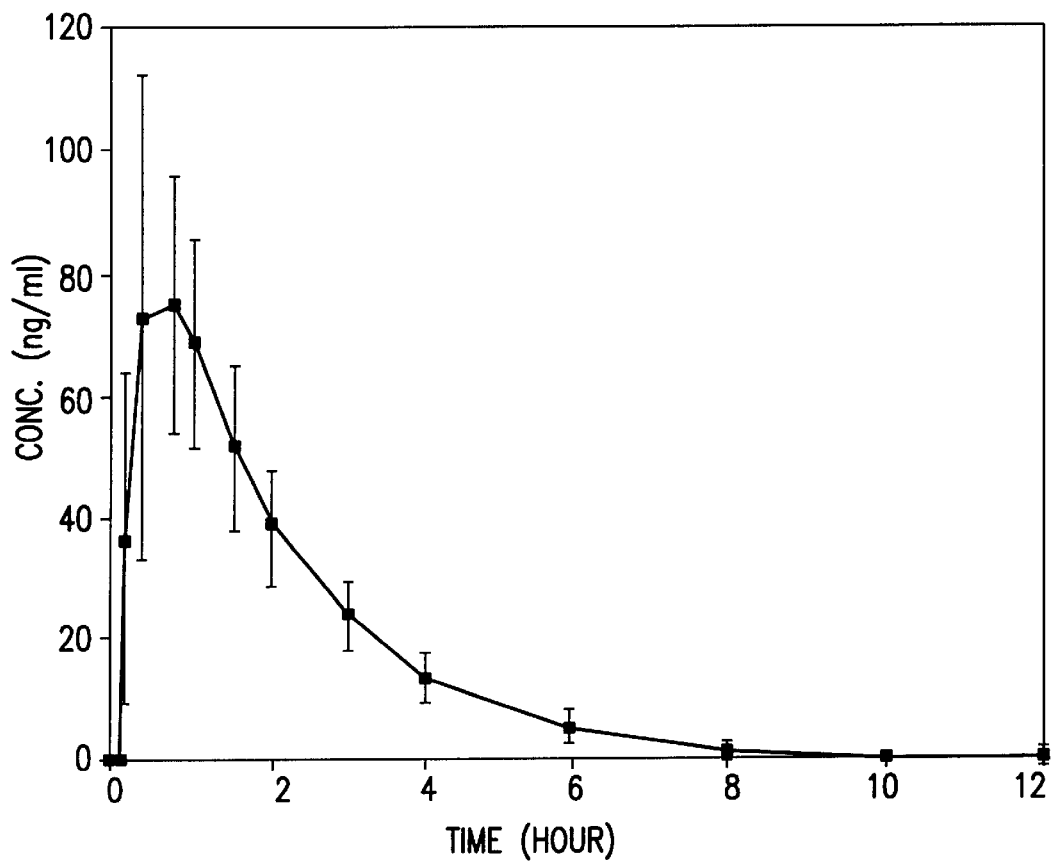
FIG. 1 is a time course of plasma nifedipine concentrations following administration of nifedipine pellets prepared according to the first embodiment (i.e., a fast-release type of nifedipine pellet which contains a particulate core and a nifedipine coating layer).

A. A Fast-Release Type of Nifedipine Pellet

The fast-release type of nifedipine pellet described in this embodiment comprises: (1) a particulate core, and (2) a nifedipine coating layer. The particulate core contains primarily an excipient and a pharmacologically acceptable carrier. The excipient can be either water-soluble or water-insoluble. The water-soluble excipient includes mannose, galactose, glucose, fructose, sucrose, lactose, maltose, dextrin, glycogen, and inulin. The preferable water-soluble excipients are sucrose and lactose, although any water-soluble saccharides (alone or in any combination) can be used for this purpose. The water-insoluble excipient(s) include, but not limited to, starch, microcrystalline cellulose, and talc. These excipients can be used alone or together in any combination. A detailed description of the formulas for making the particulate core containing water-insoluble excipients will be illustrated in (i) of Example 1 (infra). The preferred pharmacologically acceptable carrier is sucrose. A detailed description of the formulas for making the particulate core containing water-soluble excipients will be illustrated in (i) of Example 3 (infra).

The nifedipine coating layer comprises an effective amount of nifedipine. Due to the insolubility of nifedipine in water, nifedipine must be dissolved in organic solvent. Although nifedipine can be mixed with organic solvents such as acetone, alcohol, or isopropanol, it is preferable to dissolve nifedipine in an organic mixture containing acetone and alcohol in a ratio (vol/vol) of 1:1.1 to 1:4. A 0 to 30% by volume of distilled water can be added to this organic mixture.

The dissolved nifedipine (in organic solvent) is preferable to be further dispersed in an emulsified dispersing suspension which comprises at least an emulsifier, an adhesive, and a dispersant. Emulsifier such as poloxamer 188, Tween 80, and sodium lauryl sulfate, adhesive such as polyvinylpyrrolidone, hydroxypropylcellulose, methylcellulose, and hydroxypropylmethylcellulose, dispersant such as lactose, sucrose, fructose, maltose, mannose, glucose, and polyethylene glycol (PEG) (with molecular weight of 4,000, 6,000, 8,000, and 20,000) can be mixed together in any combinations and amounts. The best result can be achieved when the ratio (by weight) of particulate core and nifedipine coating layer is 1: 0.04–0.14% of nifedipine, 1–7% of emulsifier, 0.4–7% of adhesive, 0.9–11% of dispersant, 7–15% by weight of organic solvent, and 4–10% of distilled water. Detailed descriptions of the making of the nifedipine coating layer will be illustrated in (ii) of Examples 1–5 (infra).

The preferred composition for the fast-release type of nifedipine pellet comprises 20–70% by weight of the particulate core, 3 to 15% by weight of the nifedipine, 1–20% by weight of the emulsifier, 1–20% by weight of the adhesive, and 1–30% by weight of the dispersant.

B. A Prolonged-Release Type of Nifedipine Pellet

The fast-release type of nifedipine pellet can be converted to a prolonged-release type of nifedipine pellet by adding a surface coating layer on top of the nifedipine coating layer. This surface coating layer comprises at least one of the following materials: polyvinylpyrrolidone, hydroxypropylcellulose, hydroxypropylmethylcellulose, or ethylcellulose. In addition, the following plasticizers: triethyl citrate, triacetin, and diethyl phthalate, can be added to this surface coating layer to improve the flexibility of the surface coating layer. Detailed description of the formula for making the surface coating layer will be illustrated in Example 6 (infra).

C. Process for Making the Fast- or Prolonged-Release Type of Nifedipine Pellet

The nifedipine pellet can be formed using any conventional particle pelletizing apparatus, such as Glatt and Huttlin. The basic procedures for forming the pellets include: (1) spraying a fluidized material or a suspension onto an excipient or a tablet (in a drum) by means of a spraying nozzles under rotatable conditions to form wet pellets; and (2) blowing a filtered or heated air, or possibly a protective gas into the drum to dry the wet pellets.

In the case of forming a particulate core, an adhesive solution containing polyvinylpyrrolidone (dissolved in organic solvent such as isopropanol) and distilled water was sprayed onto an excipient (or a combination of several excipients) in the presence of a pharmacologically acceptable carrier by the spraying nozzles within the particle pelletizing device to form a wet pellet, followed by a blow of filtered or heated air to dry the wet pellet. Detailed descriptions of the process of making the particulate core will be illustrated in (i) of Examples 1 and 3 (infra).

In the case of covering the particulate cores with a nifedipine coating layer, an effective amount of nifedipine was dissolved in an organic solvent, such as acetone, alcohol, or isopropanol. This dissolved nifedipine solution was then sprayed onto the particulate core via the spraying nozzles in the particle pelletizing device. For better attachment of the nifedipine layer onto the particulate core, the dissolved nifedipine solution was further mixed with an emulsified dispersing suspension, which was prepared by mixing an adhesive, an emulsifier, and a dispersant together, before spraying onto the particulate core.

In the case of coating the surface coating layer on top of the nifedipine coating layer, the surface coating layer was prepared by first dissolving the surface coating materials (such as polyvinylpyrrolidone, hydroxypropylcellulose, methylcellulose, and hydroxypropylmethylcellulose) in organic solvents, followed by spraying the dissolved solution onto the nifedipine coating layer. The surface coating materials can be used alone or together in any combination. It is preferable to further add triethyl citrate, triacetin or diethyl phthalate to the surface coating material to increase the softness and flexibility of the surface coating layer to the nifedipine coating layer.

The following examples include detailed descriptions of the formation of the nifedipine pellets which serve to better illustrate the above embodiments:

EXAMPLE 1

| (i) Particulate Core Containing Water-Insoluble Excipients | |
|---|---|
| Polyvinylpyrrolidone (PVP K30) | 40 g |
| Isopropanol | 300 ml |
| Distilled Water | 200 ml |
| Sucrose | 400 g |
| Starch | 800 g |
| Talc | 900 g |

The particulate core containing water-insoluble excipients was prepared by the following procedures: (1) dissolving 40 g of PVP K30 in 300 ml of isopropanol; (2) adding and mixing 200 ml of distilled water to the dissolved PVP K30 to form an adhesive solution; (3) mixing 800 g of starch and 900 g of talc (as excipients) together; (4) putting 400 g of sucrose (as carrier) in the particle pelletizing device (Glatt); (5) spraying the adhesive solution (as shown in (2)) via spraying nozzles of the particle pelletizing device, while simultaneously adding the starch-talc (as shown in (3)) mixture, onto sucrose to form wet pellets; and (6) drying the pellets by passing a heated or filtered air through the wet pellets.

| (ii) | Nifedipine Coating Layer | |
|---|---|---|
| | Nifedipine | 63 g |
| | Poloxamer 188 | 90 g |
| | Polyvinylpyrrolidone (PVP K30) | 30 g |
| | Lactose | 60 g |
| | Acetone | 567 ml |
| | Alcohol | 633 ml |

Wherein 1,557 g of (i) were used as the particulate core containing water-insoluble excipients for the amount of nifedipine coating layer specified in (ii).

The process of coating a nifedipine coating layer onto the particulate core included the following procedures: (1) dissolving 63 g of nifedipine in 567 ml of acetone; (2) mixing the dissolved nifedipine solution with an emulsified dispersing suspension to form a nifedipine coating solution; and (3) spraying the nifedipine coating solution onto the water-insoluble particulate core via spraying nozzles within the particle pelletizing device to form the fast-release type of nifedipine pellet.

The emulsified dispersing suspension was prepared by (1) sieving 60 g of lactose through a 150 mesh (104μ); (2) mixing 30 g of polyvinylpyrrolidone (PVP K30) with 633 ml of alcohol and 90 g of poloxamer 188 to form an emulsified suspension; and (3) mixing the sieved lactose with the emulsified suspension to form the emulsified dispersing suspension.

EXAMPLE 2

(i) Particulate Core Containing Water-Insoluble Excipients

The composition of the particulate core containing the water-insoluble excipients in Example 2 was the same as that shown in (i) of Example 1.

The process of making the particulate core in Example 2 was also the same as that shown in (i) of Example 1.

| (ii) | Nifedipine Coating Layer | |
|---|---|---|
| | Nifedipine | 63 g |
| | Poloxamer 188 | 90 g |
| | Polyvinylpyrrolidone (PVP K30) | 30 g |
| | Sucrose | 120 g |
| | Acetone | 567 ml |
| | Alcohol | 633 ml |

Wherein 1,497 g of (i) were used as the particulate core containing the water-insoluble excipients for the amount of nifedipine coating layer specified in (ii).

The process of coating the nifedipine coating layer over the particulate core in Example 2 was primarily the same as that described in Example 1 except that 120 g of sucrose was used to replace 60 g of lactose as a dispersant.

EXAMPLE 3

| (i) Particulate Core Containing A Water-Soluble Excipient | |
|---|---|
| Polyvinylpyrrolidone (PVP K30) | 70 g |
| Isopropanol | 500 ml |
| Distilled Water | 200 ml |
| Sucrose | 500 g |
| Lactose | 1,800 g |

The water-soluble particulate core was formed by the following procedures: (1) dissolving 70 g of PVP K30 in 500 ml of isopropanol; (2) mixing 200 ml of distilled water with the dissolved PVP K30 to form an adhesive solution; (3) putting 500 g of sucrose (as carrier) in the particle pelletizing device (Glatt); (4) spraying the adhesive solution (as shown in (2)) via spraying nozzles of the particle pelletizing device, while simultaneously adding 1800 g of lactose (as water-soluble excipient), onto sucrose to form wet pellets; and (5) drying the pellets by passing a heated or filtered air through the wet pellets.

| (ii) | Nifedipine Coating Layer | |
|---|---|---|
| | Nifedipine | 72 g |
| | Poloxamer 188 | 108 g |
| | Polyvinylpyrrolidone | 180 g |
| | Lactose | 270 g |
| | Acetone | 720 ml |
| | Alcohol | 1,800 ml |

Wherein 1,170 g of (i) were used as the particulate core containing a water-soluble excipient for the amount of the nifedipine coating layer specified in (ii).

The process of coating the nifedipine coating layer over the particulate core in Example 3 was primarily the same as that described in Example 1, except that the ratios of polyvinylpyrrolidone, lactose, and alcohol to nifedipine in Example 3 (i.e., the ratios of polyvinylpyrrolidone, lactose, and alcohol to nifedipine in Example 3 were 2.5:1 (wt/wt), 3.8:1 (wt/wt), and 25:1 (vol/wt), respectively) were much higher than those shown in Example 1 (i.e., the ratios of polyvinylpyrrolidone, lactose, and alcohol to nifedipine in Example 1 were 0.5:1 (wt/wt), 0.1:1 (wt/wt), and 10:1 (vol/wt), respectively).

EXAMPLE 4

(i) Particulate Core Containing a Water-Soluble Excipient

The composition of the particulate core containing a water-soluble excipient in Example 4 was the same as that shown in (i) of Example 3.

The process of making the water-soluble particulate core in Example 4 was also the same as that shown in (i) of Example 3.

| (ii) | Nifedipine Coating Layer | |
|---|---|---|
| | Nifedipine | 89.25 g |
| | Tween 80 | 238 g |
| | Polyvinylpyrrolidone (PVP K30) | 238 g |
| | Lactose | 357 g |
| | Acetone | 935 ml |
| | Alcohol | 1700 ml |

Wherein 1,200 g of (i) were used as the particulate core containing a water-soluble excipient for the amount of nifedipine coating layer specified in (ii).

The process of coating the nifedipine coating layer over the particulate core in Example 4 was primarily the same as that described in Example 3 except that Tween 80 was used to replace Poloxamer 188 as emulsifier.

Example 5

(i) Particulate Core Containing a Water-Soluble Excipient

The composition of the particulate core containing a water-soluble excipient in Example 5 was the same as that shown in (i) of Example 3.

The process of making the water-insoluble particulate core in Example 5 was also the same as that shown in (i) of Example 3.

| (ii) | Nifedipine Coating Layer | |
|---|---|---|
| | Nifedipine | 81.6 g |
| | Poloxamer 188 | 224 g |
| | Polyvinylpyrrolidone (PVP K30) | 224 g |
| | Lactose | 336 g |
| | PEG 20,000 | 56 g |
| | Distilled Water | 400 ml |
| | Acetone | 928 ml |
| | Alcohol | 1,600 ml |

Wherein 1,300 g of (i) were used as the particulate core containing the water-soluble excipient for the amount of the nifedipine coating layer specified in (ii).

The process of coating the nifedipine coating layer over the particulate core in Example 5 was essentially the same as that described in Example 3 except that a PEG 20,000 solution (which was prepared by dissolving 56 g of PEG 20,000 in 400 ml of distilled water) was added to the emulsified dispersing suspension.

EXAMPLE 6

| Formulation of the Surface Coating Layer | |
|---|---|
| Ethyl cellulose | 67.2 g |
| Alcohol | 960 ml |
| Triethyl citrate | 13.4 g |

The surface coating layer can coat onto any of the nifedipine pellets described in Examples 1–5. The surface coating layer was made by dissolving 67.2 g of ethyl cellulose in 960 ml alcohol, and then mixing 13.44 g of triethyl citrate with the dissolved ethyl cellulose.

The coating process was essentially the same as those described in Examples 1–5, i.e., by spraying the surface coating layer onto the nifedipine pellets via spraying nozzles within the particle pelletizing device to form the prolonged-release type of nifedipine pellets.

The studies of the stability and % of release of nifedipine in the above Examples are shown as follows:

EXPERIMENT 1

Stability Study

The stability study of the nifedipine pellets as formulated in Examples 1–5 is shown in Table I. The stability study was conducted under the following conditions: (1) Relative Humidity—75%; (2) Temperatures—30° C., 37° C., and 45° C.; and (3) Storage Periods—0, 1, 2, 3, and 6 months. The data shown in Table I are the percentages of the remaining nifedipine at the end of the storage periods, which were measured by dividing the amount (by weight) of nifedipine after the storage period by that of nifedipine before the storage.

TABLE I

| Temp. (° C.) | Storage Time (month) | Example 1 | Example 2 | Example 3 (%) | Example 4 | Example 5 |
|---|---|---|---|---|---|---|
| — | 0 | 100.3% | 103.4% | 104.8% | 104.5% | 104.2% |
| 30 | 1 | 98.4% | 102.8% | 103.5% | 103.8% | 103.8% |
| 30 | 2 | 97.2% | 101.2% | 102.1% | 102.1% | 102.9% |
| 30 | 3 | 96.1% | 99.7% | 101.2% | 100.2% | 101.4% |

TABLE I-continued

| Temp. (° C.) | Storage Time (month) | Example 1 | Example 2 | Example 3 (%) | Example 4 | Example 5 |
|---|---|---|---|---|---|---|
| 30 | 6 | 95.4% | 97.8% | 98.9% | 98.9% | 100.2% |
| 37 | 1 | 97.8% | 102.3% | 103.1% | 103.3% | 103.8% |
| 37 | 2 | 96.0% | 100.7% | 101.9% | 102.6% | 102.8% |
| 37 | 3 | 95.1% | 98.6% | 100.6% | 101.3% | 101.1% |
| 37 | 6 | 94.3% | 96.4% | 97.8% | 98.6% | 99.6% |
| 45 | 1 | 97.4% | 102.0% | 102.8% | 103.1% | 103.6% |
| 45 | 2 | 96.5% | 100.2% | 101.3% | 101.7% | 101.9% |
| 45 | 3 | 94.3% | 97.8% | 100.1% | 100.1% | 101.0% |
| 45 | 6 | 93.1% | 95.9% | 96.9% | 98.4% | 99.3% |

As shown in Table I, the nifedipine pellets formulated in Examples 1–5 all demonstrated extremely high stability. In fact, even under the most unfavorable conditions, e.g., stored at 45° C. for 6 months, there were still more than 90% of the nifedipine pellets remained. Among Examples 1–5, it appeared that the stability of Example 1 was slightly lower than the rest of the Examples.

EXPERIMENT 2

The % of Nifedipine Release

The study of the % of release of nifedipine pellets as formulated in Examples 1–5 is shown in Table II. This study was conducted according to the standards prescribed in the U.S. Pharmacopeia (The National Formulary), Official from Jan. 1, 1995). In brief, the release rates were determined by measuring the percentages of the nifedipine released in the solution at pH 1.2 at 20 minutes versus that at 0 minute.

TABLE II

| Example No. | % of Nifedipine Released |
|---|---|
| 1 | 89.4% |
| 2 | 91.6% |
| 3 | 96.3% |
| 4 | 97.1% |
| 5 | 99.3% |

The results as shown in Table II demonstrated that at least 90% of the nifedipine in the nifedipine pellets as formulated in Examples 1–5 was released into the solution in 20 minutes. Among the five examples, Example 5 appeared to have the greatest release rate (99.3%) while Example 1 appeared to have the lowest release rate (89.4%). Because the major difference between Example 5 and the rest of the examples was that in Example 5, a PEG 20,000 solution was added, it was suggested that the PEG 20,000 solution might have contributed to the higher release rate of nifedipine in the present invention.

A time course study of the blood nifedipine concentrations prepared according to the first embodiment (i.e., a fast-release type of nifedipine pellet which contains a particulate core and a nifedipine coating layer) is shown in FIG. 1. The nifedipine pellets used in this figure contained a water-soluble particulate core and a nifedipine coating layer as formulated in Example 5. Twelve healthy males participated in this study. They were given encapsulated nifedipine pellets via oral administration. Blood nifedipine concentrations were monitored by High Performance Liquid Chromatograph (HPLC) using Column LiChroCART® 125-4, 4*125 mm, 5 μm (Merck, Lot. L228433) at UV wavelength 340 nm at 0.005 AUFS. The column used a mobile phase which contained 0.1 M $KH_2PO_4$ (pH 4.0): $CH_3CN$=48:35 (vol/vol). The flow rate of the column was 1.0 ml/min and the column pressure was maintained at 70 bar.

As shown in FIG. 1, most of the nifedipine was released to the blood within the first two hours of the nifedipine administration with a peak at 30 minutes. The nifedipine can be maintained in blood for approximately 8 hours.

Figure 2:
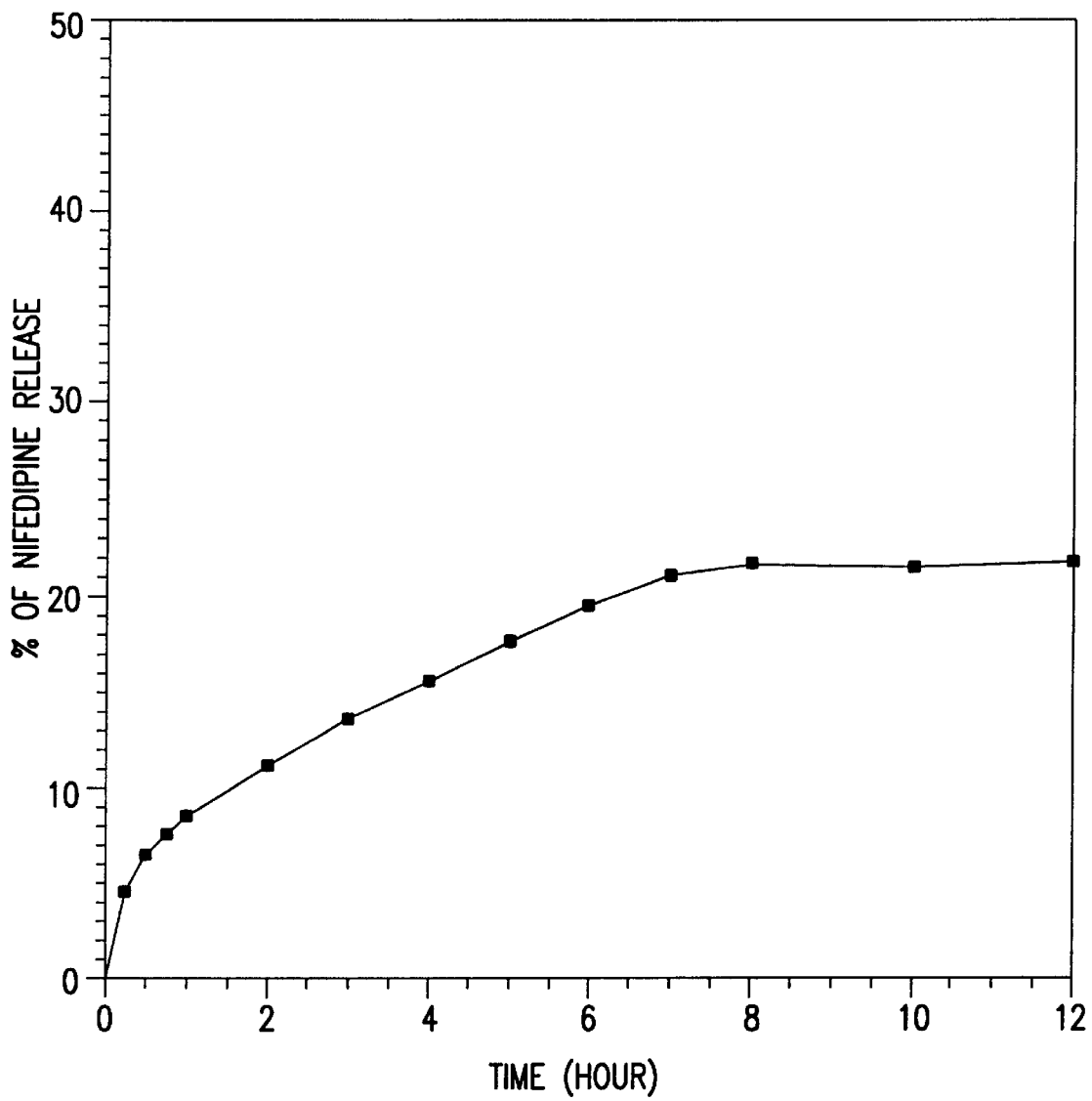
FIG. 2 is a time course which measures the % of release for nifedipine pellets prepared according to the second embodiment (i.e., a prolonged-release type of nifedipine pellet which contains a particulate core, a nifedipine coating layer, and a surface coating layer) of the invention.

A time course study of the % of release of the prolonged-release type of nifedipine (i.e., containing a particulate core, a nifedipine coating layer, and a surface coating layer) is shown in FIG. 2. The % of release was conducted by measuring the percentages of the nifedipine released in the solution at pH 1.2 at different time points versus that at 0 minute using HPLC method. The nifedipine pellet for this study was prepared according to the formulation set forth in Example 6.

Contrasting to the results shown in Table II where more than 90% of nifedipine was released after 20 minutes in a solution having a pH at 1.2, only 6.5% of nifedipine was released from nifedipine pellets containing a surface coating layer after 30 minutes at pH 1.2. In addition, the release of nifedipine in this study plateaued at 21% between 7 hours and 12 hours, notwithstanding the fact that these nifedipine pellets had the same underlining particulate core and nifedipine coating layer as those described in Table II.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A nifedipine pellet comprising:
    a particulate core; and
    a nifedipine coating layer covering said particulate core, wherein said nifedipine coating layer comprises an effective amount of nifedipine dissolved in an organic solvent;
    said dissolved nifedipine being mixed with an emulsifier, an adhesive, a dispersant, and water to form said nifedipine coating layer.

2. The nifedipine pellet according to claim 1, wherein said particulate core comprises a water-soluble excipient and a pharmacologically acceptable carrier, wherein said water-soluble excipient is at least a water-soluble saccharide selected from the group consisting of mannose, galactose, glucose, fructose, sucrose, lactose, maltose, dextrin, glycogen, and inulin.

3. The nifedipine pellet according to claim 2, wherein said pharmacologically acceptable carrier is sucrose.

4. The nifedipine pellet according to claim 1, wherein said particulate core comprises a water-insoluble excipient, wherein said water-insoluble excipient is at least one selected from the group consisting of starch, microcrystalline cellulose, and talc.

5. The nifedipine pellet according to claim 1, wherein said organic solvent is at least one selected from the group consisting of acetone, alcohol, and isopropanol.

6. The nifedipine pellet according to claim 1, wherein said organic solvent comprises acetone and alcohol in a ratio (volume/volume) of 1:1.1 to 1:4.

7. The nifedipine pellet according to claim 6, wherein said organic solvent further comprises 0 to 30% by volume of distilled water.

8. The nifedipine pellet according to claim 1, wherein a weight ratio of said particulate core and said nifedipine coating layer is 1: 0.04–0.14% by weight of nifedipine, 1–7% by weight of emulsifier, 0.4–7% of adhesive, 0.9–11% of dispersant, 7–15% by weight of organic solvent, and 4–10% of distilled water.

9. The nifedipine pellet according to claim 1, wherein said nifedipine pellet comprises 20 to 70% by weight of the particulate core, 3 to 15% by weight of the nifedipine, 1–20% by weight of the emulsifier, 1–20% by weight of the adhesive, and 1–30% by weight of the dispersant.

10. The nifedipine pellet according to claim 1, wherein said emulsifier is at least one selected from the group consisting of poloxamer 188, Tween 80, and sodium lauryl sulfate.

11. The nifedipine pellet according to claim 1, wherein said adhesive is at least one selected from the group consisting of polyvinylpyrrolidone, hydroxypropylcellulose, methylcellulose, and hydroxypropylmethylcellulose.

12. The nifedipine pellet according to claim 1, wherein said dispersant is at least one selected from the group consisting of lactose, sucrose, fructose, maltose, mannose, glucose, and polyethylene glycol, wherein said polyethylene glycol has a molecular weight ranged between 6000 and 20,000.

13. The nifedipine pellet according to claim 1, further comprising a surface coating layer which covers said nifedipine coating layer, wherein said surface coating layer comprises at least one selected from the group consisting of polyvinylpyrrolidone, hydroxypropylcellulose, hydroxypropylmethylcellulose, and ethylcellulose.

14. The nifedipine pellet according to claim 13, wherein said surface coating layer further comprises at least one plasticizer selected from the group consisting of triethylcitrate, triacetin, and diethyl phthalate.

15. A method of making a nifedipine pellet comprising the steps of:
    making a particulate core; and
    spraying a nifedipine coating layer according to claim 1 onto said particulate core.

16. The method of making a nifedipine pellet according to claim 15, further comprising a step of:
    spraying a surface coating layer onto said nifedipine coating layer.

17. The method of making a nifedipine pellet according to claim 15, wherein making said particulate core comprises the steps of:
    dissolving polyvinylpyrrolidone in an organic solvent;
    mixing said dissolved polyvinylpyrrolidone with distilled water to form an adhesive solution;
    mixing a pharmacologically acceptable carrier and an excipient in a particle pelletizing device, wherein said excipient is water-soluble or water-insoluble; and
    spraying said adhesive solution onto said pharmacologically acceptable carrier and said excipient.

18. The method of making a nifedipine pellet according to claim 15, wherein making of said nifedipine coating layer comprises the steps of:
    preparing an emulsified dispersing suspension by mixing an adhesive, an emulsifier, and a dispersant together;
    dissolving nifedipine in an organic solvent;
    mixing said dissolved nifedipine with said emulsified dispersing suspension to form a nifedipine coating solution; and
    spraying said nifedipine coating solution onto said particulate core.

19. The method of making a nifedipine pellet according to claim 16, wherein making of said surface coating layer comprises the steps of:
    dissolving a surface coating material in alcohol or distilled water, wherein said surface coating material is at least one selected from the group consisting of polyvinylpyrrolidone, hydroxypropylcellulose, hydroxypropylmethylcellulose, and ethylcellulose; and
    spraying said alcohol- or distilled water-dissolved surface coating material onto said nifedipine coating layer of said nifedipine pellet.

20. The method of making a nifedipine pellet according to claim 19, further comprising a step of adding triethyl citrate, triacetin or diethyl phthalate to said surface coating material.

21. The nifedipine pellet according to claim 9, wherein said nifedipine pellet comprises no less than 3% and no more than 20% by weight of the emulsifier.

22. The nifedipine pellet according to claim 10, wherein said emulsifier is poloxamer 188.

* * * * *